United States Patent [19]

Eplett, Jr.

[11] Patent Number: 5,236,422
[45] Date of Patent: Aug. 17, 1993

[54] ANTISEPTIC URINARY CATHETER CUFF

[76] Inventor: James D. Eplett, Jr., 24426 Peacock St., El Torro, Calif. 92630

[21] Appl. No.: 719,475

[22] Filed: Jun. 24, 1991

[51] Int. Cl.⁵ .......................................... A61M 25/00
[52] U.S. Cl. ..................................... 604/265; 604/174
[58] Field of Search .................. 604/93, 264, 265, 101, 604/174, 178; 128/207.15

[56] References Cited

U.S. PATENT DOCUMENTS

| | | | |
|---|---|---|---|
| 2,687,131 | 8/1954 | Raiche | 604/101 |
| 2,936,760 | 5/1960 | Gants | 604/101 X |
| 3,593,713 | 7/1971 | Bogoff et al. | 604/265 X |
| 3,606,889 | 9/1971 | Arblaster | 604/265 X |
| 3,699,956 | 10/1972 | Kitrilakis et al. | 604/265 X |
| 4,495,948 | 1/1985 | Shapiro | 128/207.15 |
| 4,676,782 | 6/1987 | Yamamoto et al. | 604/175 |
| 4,755,171 | 7/1988 | Tennant | 604/93 |
| 4,784,647 | 11/1988 | Gross | 604/178 |
| 5,049,140 | 9/1991 | Brenner et al. | 604/266 |
| 5,176,638 | 1/1993 | Michael | 604/101 |

Primary Examiner—John D. Yasko
Assistant Examiner—Adam J. Cemak
Attorney, Agent, or Firm—Knobbe, Martens, Olson & Bear

[57] ABSTRACT

A cylindrical antiseptic cuff with an inner shaft to be placed along a urinary catheter within the patient's distal urethra for preventing infection associated with bacterial migration along the catheter surface. In a preferred embodiment, a thin infusion port is provided for charging or repleting the cuff with antimicrobial substance. The antiseptic cuff imparts a sterile, occlusive interface between catheter shaft and distal urethral mucosa, and precludes incidental sliding movements of the catheter. In an alternative embodiment, an antiseptic cuff is constructed of several concentric layers of antiseptic material, sequential outer layers being manually removable for eradicating surface pathogens while the catheter remains in position. A longitudinally directed cleft may be implemented to afford opening of the cuff for lengthwise mounting onto a catheter.

3 Claims, 3 Drawing Sheets

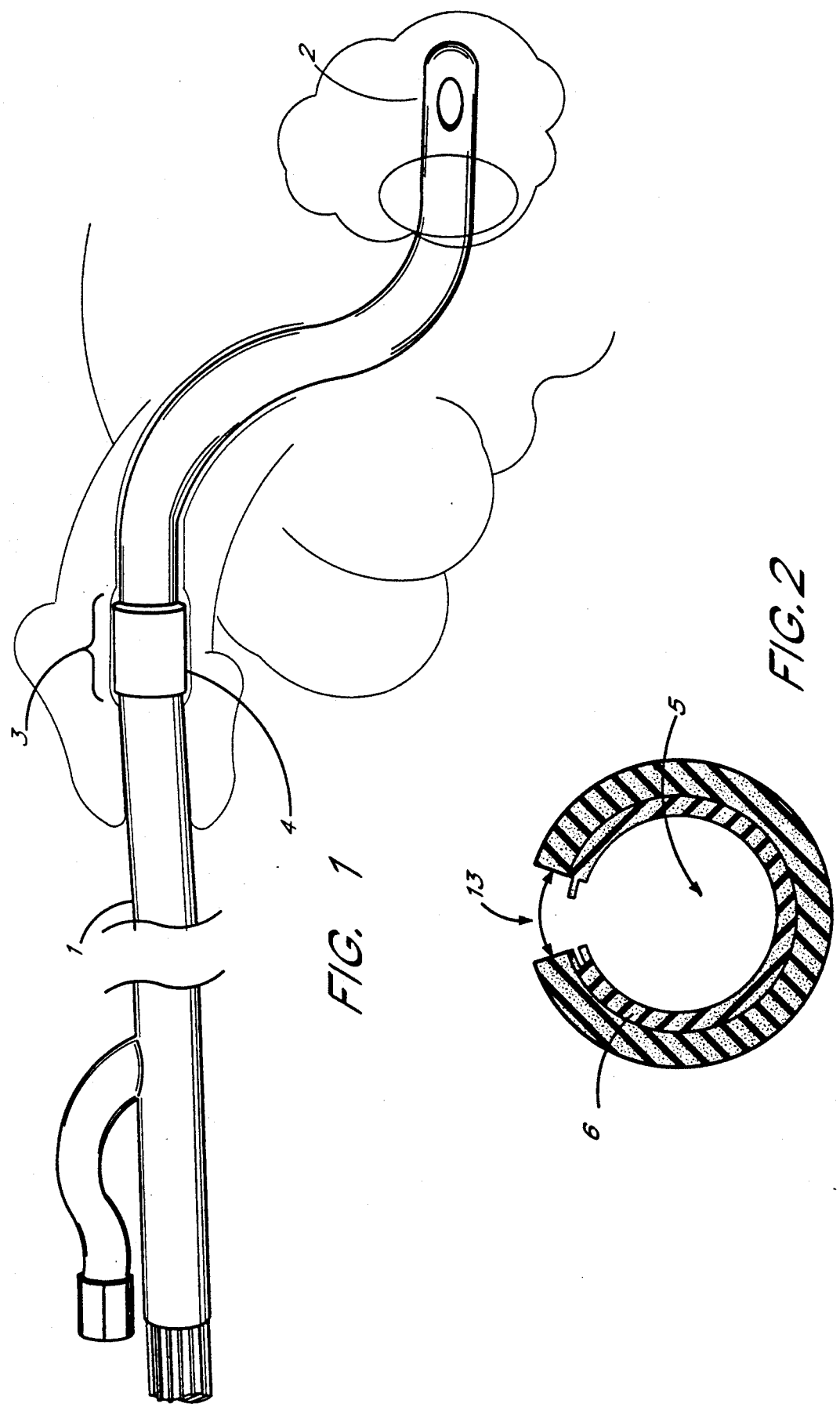

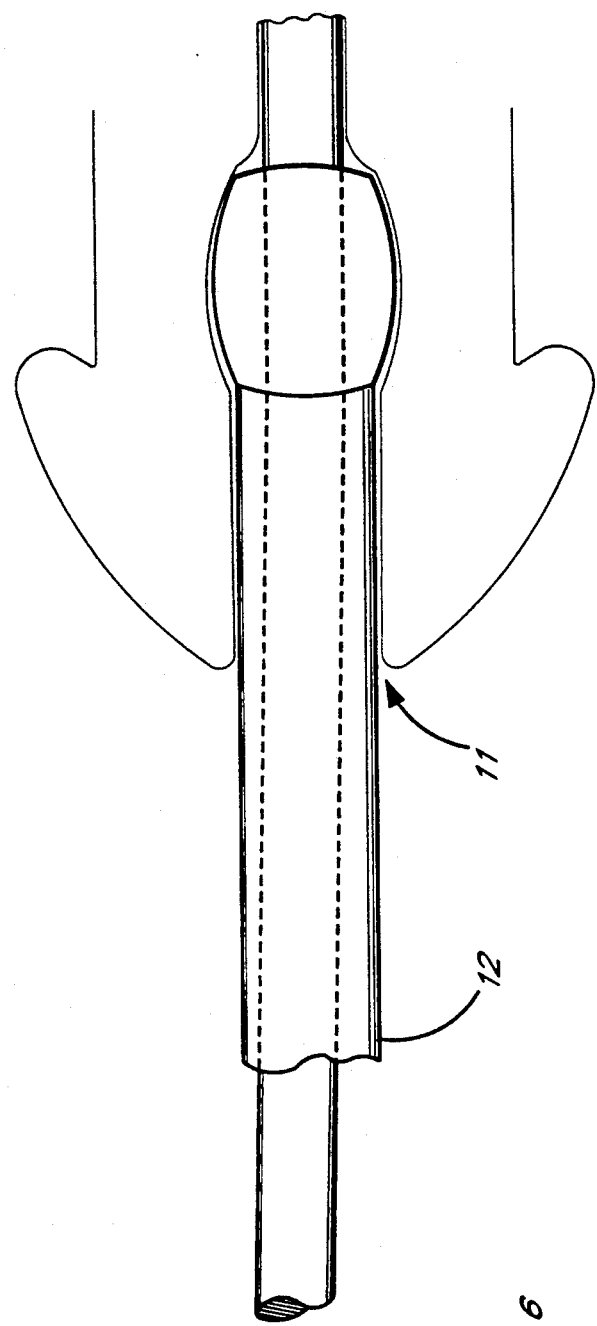
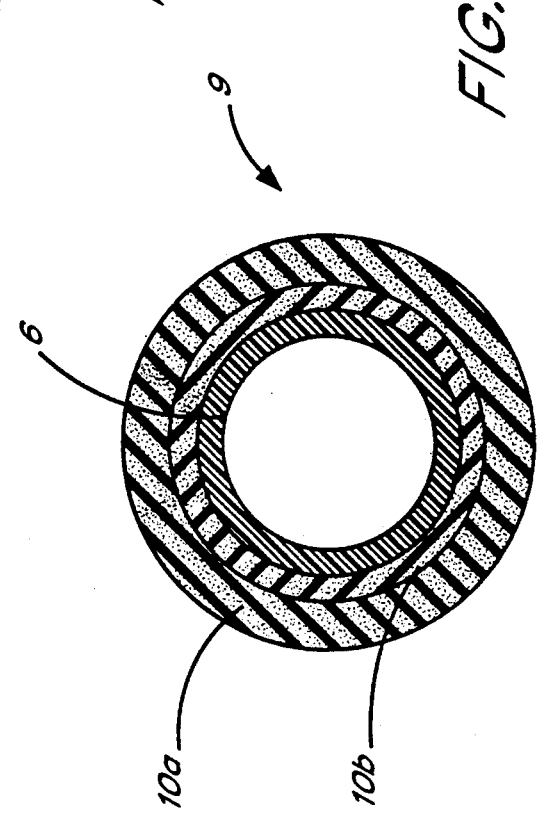
FIG. 5
FIG. 4

ANTISEPTIC URINARY CATHETER CUFF

BACKGROUND OF THE INVENTION

Urinary catheterization is a routine procedure in the hospital and chronic care settings, and is associated with a significant risk of infection. The incidence of catheter-associated urinary tract infection approaches 50% after three days of continuous catheterization, according to some epidemiologic studies, and urinary tract infections account for the majority of nosocomial infections. Complications of urinary tract infection include bacteremia, pyelonephritis, antibiotic toxicity and renal failure, with resulting morbidity and mortality and direct costs exceeding $500 Million per year in the hospital setting alone.

In a closed sterile drainage system, bacteria can be transported from the urethral tip to the bladder during catheter insertion, and after catheter insertion migrate from the urethral tip to the bladder along the outside surface of the catheter shaft at its interface with the urethral mucosa. Prior art is replete with urethral catheters which deliver antiseptic materials to the urethra/catheter interface. U.S. Pat. No. 3,598,127 issued Aug. 10, 1971 to the name of James G. Wepsic, discloses a nonpermeable catheter tube with several peripherally located grooves filled with medicament, and a sheath covering the grooves which is permeable to the medicament. U.S. Pat. No. 4,623,329 presents a catheter tube and other permeable sleeve containing a concentric reservoir of antimicrobial fluid, the sleeve allowing controlled passage of the fluid to the catheter surface.

Other workers have altered the catheter tube surface composition to incorporate microbiocidal substances. U.S. Pat. No. 4,515,593 introduces a catheter comprised of hydrophobic elastomer and coated with a hydrophilic elastomer for incorporation of antimicrobial material. U.S. Pat. No. 4,539,234 disclosed a catheter composed of polymer base material with antimicrobial substance chemically bonded to the catheter wall.

Prior art urinary catheters have generally been designed for dispensing antimicrobial agents to the catheter surface. However, sliding movements of the catheter displace pathogens along the tube surface toward the bladder, and fluid motion may paradoxically expedite bacterial movement within the potential space between urethral mucosa and catheter surface. In addition, the chemical agent may not be sufficiently concentrated in areas of bacterial inoculation, and large inoculations from the urethral tip can circumvent such chemical barriers. In general, prior art catheters have been relatively complex in design and costly to construct, as well.

U.S. Pat. No. 4,784,647 introduces a foam pad treated with antimicrobial material which contacts the urethral meatus to minimize bacterial proliferation at this site. While colonization of bacteria is reduced, viable pathogens within the distal urethra can avoid contacting the antimicrobial agent and may access the bladder. Additionally, bacteria at the urethral tip and meatus could access the urethra and move proximally as contact between pad and meatus is interrupted during movements of patent and catheter (an antislip mechanism is provided in this invention to minimize interruptions in contact, however). Relatively large concentrations of bacteria at the urethral tip may challenge the barrier presented by the pad, with greater probability of success in bypassing it.

It is an object of the present invention to provide an antiseptic cuff for a urinary catheter for minimizing bacterial viability within the urethra, thereby preventing infection. A physical and chemical barrier to bacterial migration along a catheter tube surface is provided which also attenuates catheter movements within the urethra and is simply to manufacture and to apply.

DISCLOSURE OF THE INVENTION

According to the present invention, an antiseptic cuff to be situated along a urinary catheter within the patient's distal urethra for preventing infection. The cylindrical antiseptic cuff is constructed of biocompatible sponge or foam material which may be charged with an antimicrobial substance. disposed circumferentially about the catheter shaft, the cuff has a hollow inner core for advancing it manually along the catheter shaft. The cuff is positioned at a distance from the catheter tip corresponding with the distal urethral site when the catheter tip is in the bladder. A snug fit is maintained between cuff and catheter, and the cuff expands when charged with antimicrobial material sufficiently to intimately contact surrounding tissues without exerting undue pressure. The cuff therefore imparts an occlusive sterile interface between the catheter and urethral mucosa, and attenuates sliding movements of the catheter.

In a preferred embodiment, a thin infusion port is connected from outside the urethra with its tip disposed within the cuff for charging or repleting antimicrobial agent. Antimicrobial fluid infused through the outside portal flows through the infusion port to the cuff and is retained there. The infusion port may be manufactured as a removable cuff extension.

In an alternative embodiment, the antiseptic cuff may be constructed of several concentric layers of material, whereby successive outer surface layers are removable by pulling a tab connected to each layer while the catheter remains in position. Any bacteria managing to remain viable at the cuff surface are removed with each successive layer and the urethra contracts around each new outer layer. This provides additional means for pathogen eradication, particularly when a urinary catheter remains in position for relatively long periods.

The antiseptic cuff may provide a sterile leading edge when inserted together with the catheter tip into the urethral meatus. Alternatively, the catheter may be inserted in standard fashion and the cuff subsequently advanced to the distal urethral location. A think rigid extension may be employed to advance the cuff along the catheter to a predetermined distance within the distal urethra following catheter insertion, or the infusion port may assume this function. In a preferred embodiment, a longitudinally directed cleft may be implemented during construction to afford opening of the cuff for lengthwise mounting onto the catheter. The latter feature obviates manipulation of the catheter when removing or replacing the antiseptic cuff.

DESCRIPTION OF PREFERRED EMBODIMENTS

Figure depicts an indwelling urinary catheter comprised of conventional elements including an elongated shaft 1 in the form of a drainage tube, one end of which is adapted for connection to a drainage conduit. The tube tip 2 at the opposing end is located in the bladder, comprised of drainage perforations and a balloon for retaining the tip 2 within the bladder (the male urethra is diagrammed in the interest of clarity).

An antiseptic cuff 4 is shown disposed circumferentially about the catheter shaft 1 at a distance from the tip 2, corresponding to the distal urethra 3. The cuff 4 is cylindrical and expands slightly when charged with antimicrobial fluid. Constructed of biocompatible sponge, foam or similar porous biocompatible material, the cuff 4 retains antiseptic material and functions by forming a sterile occlusive interface between catheter shaft 1 and surrounding tissue surfaces.

FIG. 2 shows the antiseptic cuff 4 in cross-section, comprised of an inner hollow core 5 for sliding over the catheter shaft 1. The core 5 diameter is slightly larger than the shaft 1 diameter, imparting a snug fit between cuff 4 and shaft An inner hollow shaft 6 of plastic, polyurethane or rubber may be included during construction to add rigidity and reduce spontaneous movements of the cuff 4 along the catheter shaft 1. The antiseptic cuff 4 may therefore be manually advanced along the catheter shaft 1, but resists spontaneous sliding associated with incidental movements of the patient and external tubing connected to the catheter.

The cuff 4 is positioned on the catheter shaft 1 such that it contacts the distal urethral mucosa 3 where pathogens may access the urinary tract, ascending along the catheter surface. Charged with antimicrobial material, the cuff 4 therefore creates a sterile occlusive interface with distal urethral mucosa 3, maintains intimate contact without exerting undue pressure on surrounding tissue, and abates catheter sliding conducive to bacterial migration. Bacterial proliferation within the urinary tract is prevented and pathogens migrating along catheter and urethral mucosal surfaces are eradicated.

An infusion port 7 is depicted in FIG. 3, connected with its tip 7a disposed within the cuff 4 and an opposing end 7b adapted for syringe infusion of antimicrobial fluid. The tip 7a comprises a single closed end and a plurality of eyelets 8 located within the cuff 4 segment. Antimicrobial fluid introduced through the infusion port 7 flows through the eyelets 8 and is dispersed in all directions through porous channels within the cuff 4 substance. The infusion port 7 may be manufactured as a removable cuff implement.

In another embodiment illustrated in FIG. 4, an antiseptic cuff 9 comprised of the previously described elements is constructed of several concentric layers 10 of biocompatible sponge or foam which is charged with microbiocidal material. The outer surface layer 10a is removable following catheter placement by manually pulling a tab or similar attachment and stripping it away from the cuff layer below. Following removal of the outer layer 10a, the urethra contracts around the cuff 9 to contact the new outer surface layer 10b. The new outer layer 10b may subsequently be removed in similar fashion. If any bacteria can remain viable at the cuff 9 surface, they are removed along with each successive cuff layer 10 at desired time intervals while the catheter remains in position.

During catheter placement, the cuff 4 may be employed to provide a sterile leading edge when inserted simultaneously with the catheter tip 2 into the urethral meatus 11. The catheter is subsequently advanced manually through the hollow inner core 5 of the cuff 4 toward the bladder, the cuff 4 ultimately positioned within the distal urethra 3. Alternatively, the catheter can be inserted in standard fashion with the antiseptic cuff 4 initially positioned around the catheter neck. The cuff 4 is then advanced into the meatus 11 to the distal urethra 3. A think rigid cuff extension 12 may be included during construction to enable manual advancement of the cuff 4 along the catheter to a predetermined distance within the urethra (or a rigid infusion port 7 could assume this function). In addition, a longitudinally directed cleft 13 may be constructed to afford opening of the cuff 4 and lengthwise mounting onto the catheter shaft 1 while the latter remains in position.

BRIEF DESCRIPTION OF THE DIAGRAMS

FIG. 1 depicts the antiseptic cuff mounted to a urinary catheter.

FIG. 2 illustrates the antiseptic cuff in cross-section.

FIG. 4 shows an antiseptic cuff comprising several concentric removable layers of material.

FIG. 5 illustrates the rigid cuff extension of an alternative embodiment of the invention.

Figure 3:
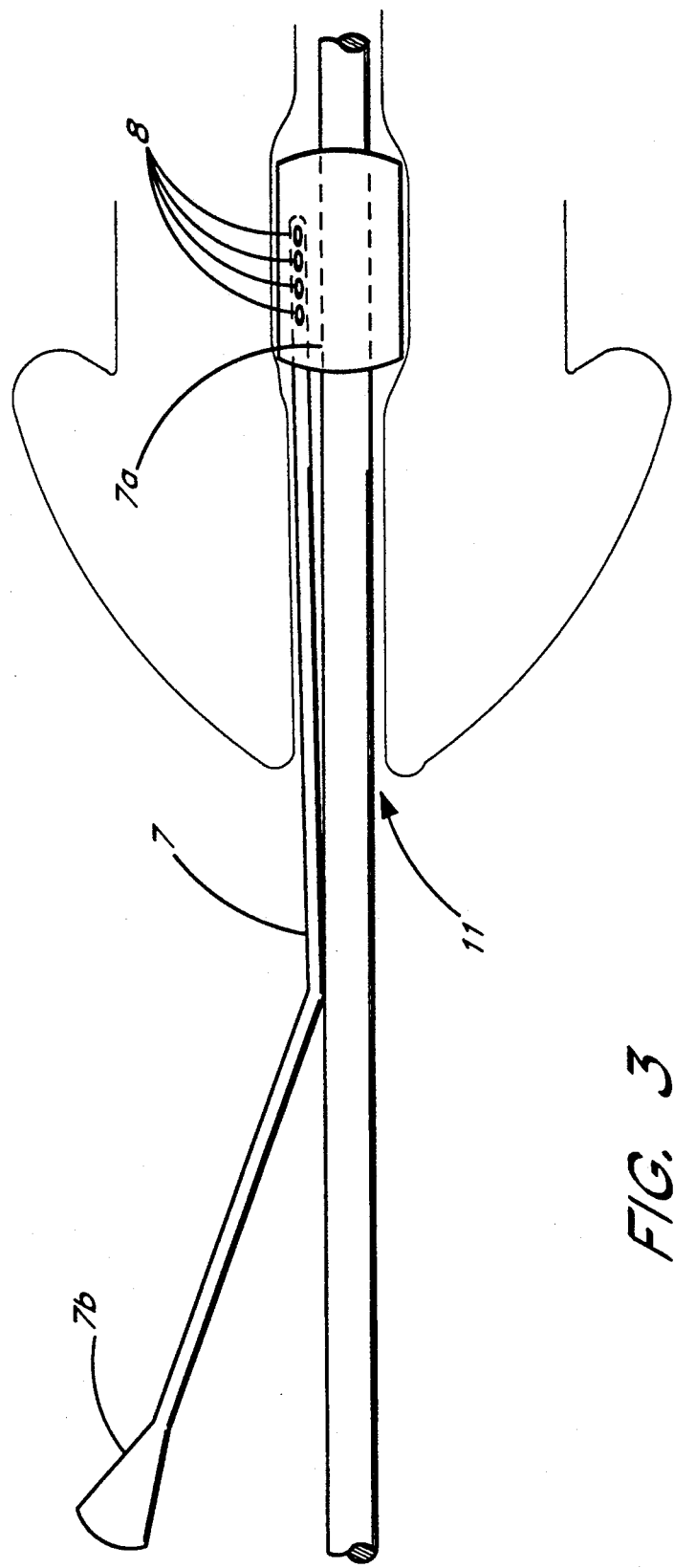
FIG. 3 is an enlarged representation of the antiseptic cuff and infusion port in position within the urethra.

What is claimed is:

1. An antiseptic cuff for attachment to a urinary catheter for preventing infection associated with bacterial migration along the catheter surface, comprising:
   an annular cylinder of resilient biocompatible material having capacity to retain antimicrobial substance; and
   a hollow inner core for mounting said annular cylinder around a catheter shaft, wherein said annular cylinder is comprised of a plurality of concentric layers of material, each layer being manually removable from outer to inner layer with the catheter remaining in position.

2. The antiseptic cuff as defined in claim 1, wherein said resilient biocompatible material comprises a biocompatible sponge foam.

3. The antiseptic cuff as defined in claim 1, additionally comprising at least one infusion port connected to said annular cylinder, wherein said infusion port is adapted for infusion of said antimicrobial substance into said annular cylinder of resilient biocompatible material.

* * * * *